(12) United States Patent
Erlebacher

(10) Patent No.: US 7,933,661 B2
(45) Date of Patent: Apr. 26, 2011

(54) LEAD RETENTION MEANS

(75) Inventor: Jay A. Erlebacher, Tenafly, NJ (US)

(73) Assignee: Medtronic, Inc., Minneapolis, MN (US)

( * ) Notice: Subject to any disclaimer, the term of this patent is extended or adjusted under 35 U.S.C. 154(b) by 814 days.

(21) Appl. No.: 11/750,632

(22) Filed: May 18, 2007

(65) Prior Publication Data

US 2007/0270928 A1    Nov. 22, 2007

Related U.S. Application Data

(63) Continuation-in-part of application No. 10/771,643, filed on Feb. 4, 2004, now Pat. No. 7,212,869.

(51) Int. Cl.
*A61N 1/05* (2006.01)

(52) U.S. Cl. ........ 607/126; 607/116; 607/118; 607/128; 607/130; 607/131; 607/132; 607/122; 607/123; 600/373; 600/374; 600/375

(58) Field of Classification Search .............. 607/4, 126, 607/116–118, 128, 130–131, 122–123; 600/376–375
See application file for complete search history.

(56) References Cited

U.S. PATENT DOCUMENTS

| | | | |
|---|---|---|---|
| 3,835,864 A * | 9/1974 | Rasor et al. ............... 607/36 |
| 3,939,843 A | 2/1976 | Smyth |
| 4,272,577 A | 6/1981 | Lyng |
| 4,419,819 A | 12/1983 | Dickhudt et al. |
| 4,540,195 A | 9/1985 | Smith-Johannsen |
| 4,550,737 A | 11/1985 | Osypka |
| 4,651,751 A * | 3/1987 | Swendson et al. ........... 607/122 |
| 4,796,643 A | 1/1989 | Nakazawa et al. |
| 4,827,940 A | 5/1989 | Mayer et al. |
| 4,841,971 A | 6/1989 | Hess |
| 4,876,109 A | 10/1989 | Mayer et al. |
| 4,957,118 A | 9/1990 | Erlebacher |
| 5,011,494 A | 4/1991 | von Recum et al. |
| 5,168,880 A * | 12/1992 | Sogawa et al. ............. 607/102 |
| 5,219,361 A | 6/1993 | von Recum et al. |
| 5,425,362 A * | 6/1995 | Siker et al. ................ 600/376 |
| 5,433,731 A * | 7/1995 | Hoegnelid et al. ............ 607/5 |
| 5,580,699 A | 12/1996 | Layman et al. |
| 5,653,690 A | 8/1997 | Booth et al. |
| 5,733,322 A | 3/1998 | Starkebaum |
| 5,797,905 A * | 8/1998 | Fleischman et al. ......... 606/41 |
| 5,865,843 A | 2/1999 | Baudino |
| 5,911,733 A | 6/1999 | Parodi |
| 5,957,965 A | 9/1999 | Moumane et al. |
| 5,984,896 A * | 11/1999 | Boyd ........................ 604/175 |

(Continued)

OTHER PUBLICATIONS

Product Sheet, http://www.biotronik.de/sixcms/detail.php/6535 http://www.biotronik.de/sixcms/detail.php/571.

(Continued)

*Primary Examiner* — Carl H Layno
*Assistant Examiner* — Paula J Stice
(74) *Attorney, Agent, or Firm* — Stephen W. Bauer; Reed A. Duthler

(57) ABSTRACT

A coiled member of a medical device extends along a length of an elongate body of the device. A surface of the coiled member extends at an angle, with respect to a longitudinal axis of the body, from a first edge to a second edge, toward the proximal end of the body, such that the first edge of the surface is disposed in close proximity to the body and the second edge of the surface is spaced apart from the body.

19 Claims, 12 Drawing Sheets

U.S. PATENT DOCUMENTS

| | | |
|---|---|---|
| 5,999,858 A | 12/1999 | Sommer et al. |
| 6,006,122 A | 12/1999 | Smits |
| 6,136,021 A | 10/2000 | Tockman et al. |
| 6,144,882 A | 11/2000 | Sommer et al. |
| 6,263,249 B1 | 7/2001 | Stewart et al. |
| 6,293,907 B1 | 9/2001 | Axon et al. |
| 6,304,786 B1 | 10/2001 | Heil, Jr. et al. |
| 6,511,452 B1 | 1/2003 | Rejai et al. |
| 6,549,811 B2 | 4/2003 | Stewart et al. |
| 6,575,933 B1 * | 6/2003 | Wittenberger et al. .. 604/101.02 |
| 6,594,515 B2 | 7/2003 | Watson |
| 6,599,310 B2 | 7/2003 | Leung et al. |
| 6,767,339 B2 | 7/2004 | Reydel |
| 6,846,296 B1 | 1/2005 | Milbocker et al. |
| 2001/0021866 A1 * | 9/2001 | Dobak et al. ................. 607/105 |
| 2001/0041874 A1 | 11/2001 | Reydel |
| 2002/0035379 A1 * | 3/2002 | Bardy et al. ...................... 607/4 |
| 2003/0171742 A1 * | 9/2003 | Mihalik et al. ................. 606/22 |
| 2003/0199961 A1 | 10/2003 | Bjorklund et al. |
| 2003/0199962 A1 | 10/2003 | Struble et al. |
| 2004/0059401 A1 | 3/2004 | Ollivier |
| 2004/0111139 A1 * | 6/2004 | McCreery ..................... 607/117 |
| 2004/0122498 A1 | 6/2004 | Zhang et al. |
| 2005/0004640 A1 | 1/2005 | Kolberg |
| 2005/0171588 A1 | 8/2005 | Wahlstrom et al. |
| 2006/0074470 A1 | 4/2006 | Bartels et al. |

OTHER PUBLICATIONS

Product Sheet, Guidant Corporation, http://www.guidant.com/products/producttemplates/crm/easytrak.shtml#Nominal%20Specifications (2004).

http://www.amonline.net.au/fishes/what/scales/index.htm, "Fish Scales," Australian Museum online. p. 1-2.

International Search Report, PCT/US2008/064108, Sep. 15, 2008, 6 pages.

* cited by examiner

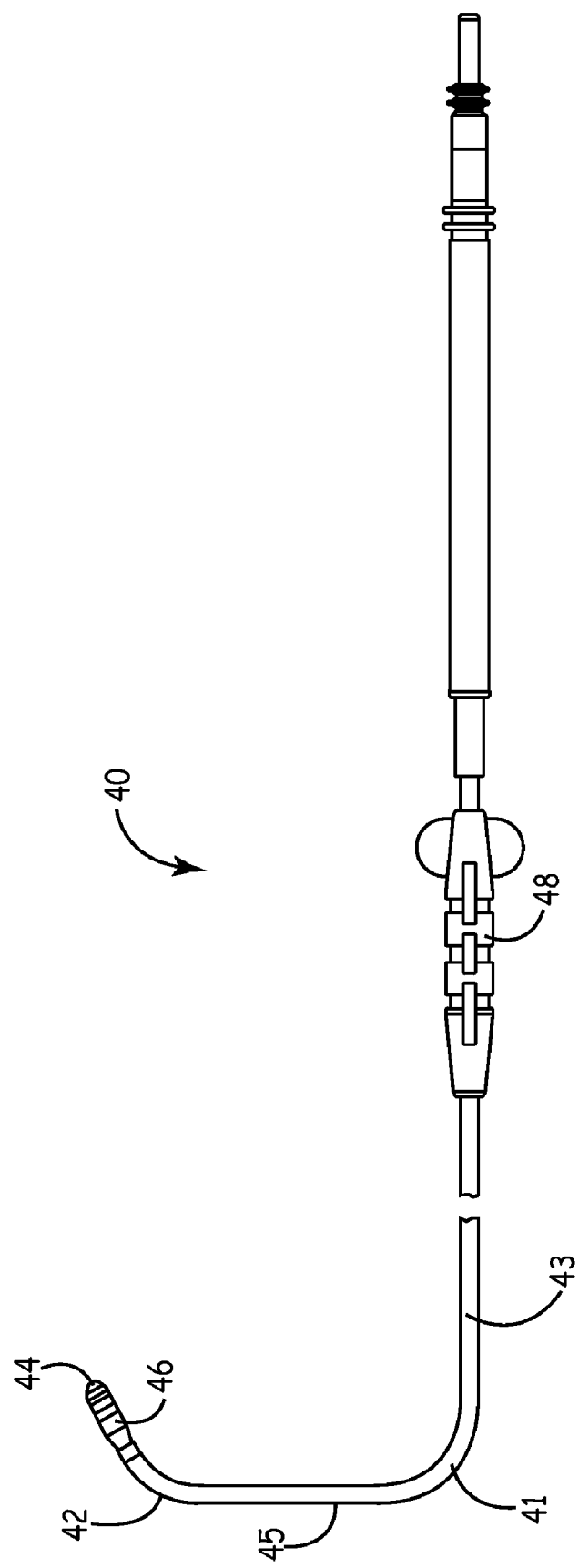

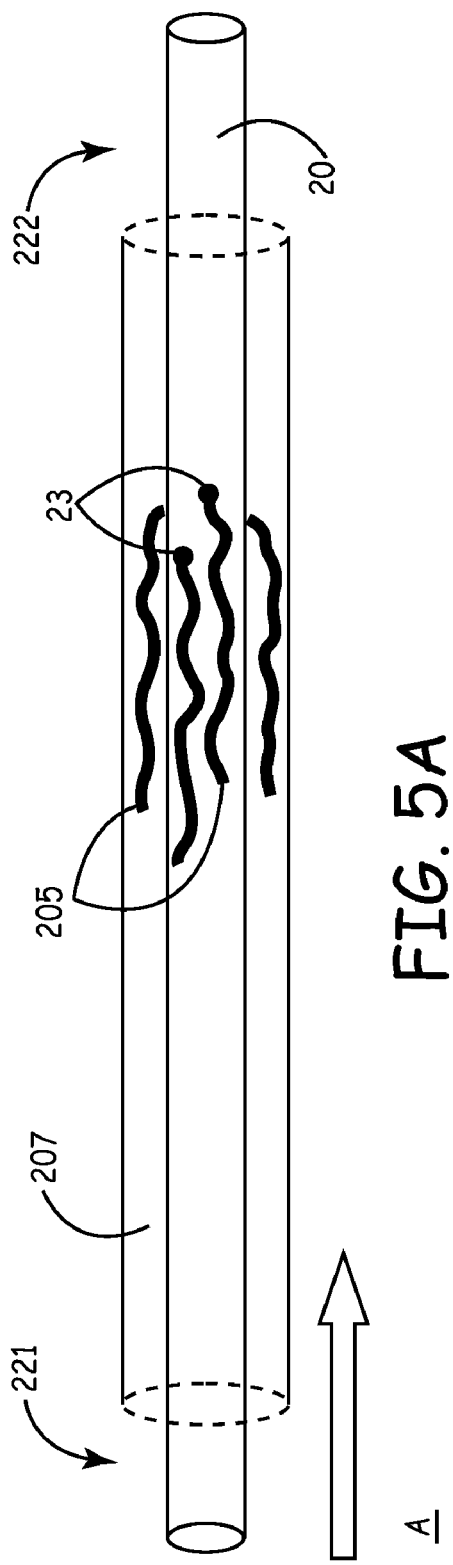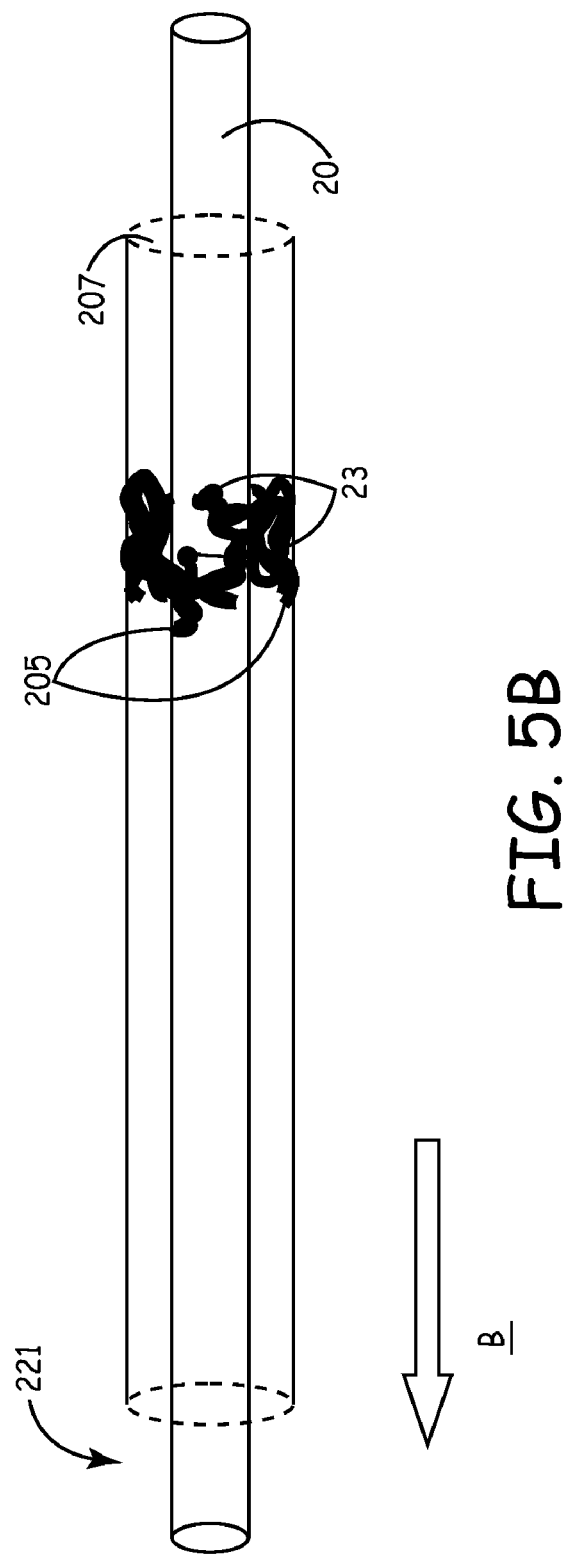
FIG. 5A
FIG. 5B

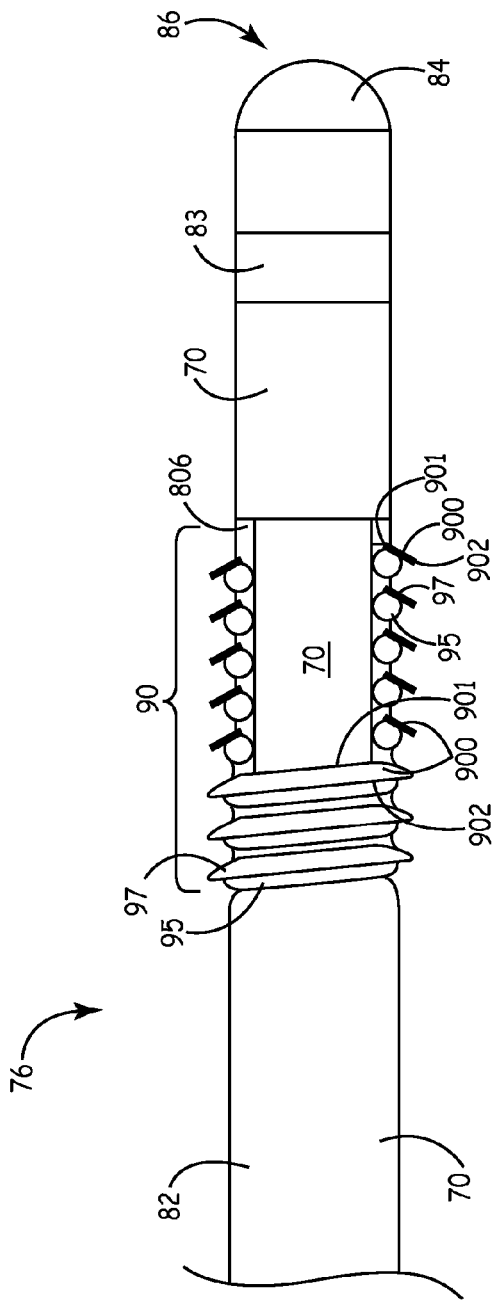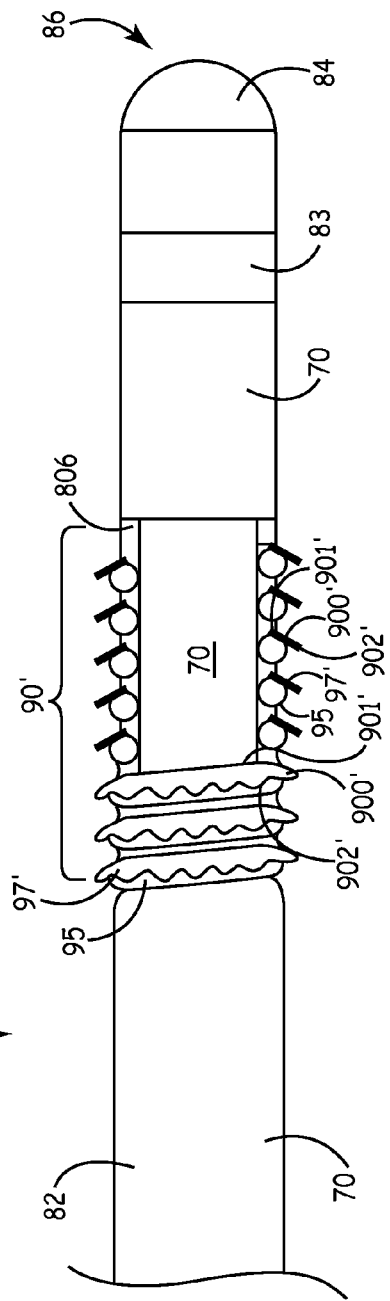

LEAD RETENTION MEANS

RELATED APPLICATION

The present application is a continuation-in-part of Ser. No. 10/771,643, filed Feb. 4, 2004, now U.S. Pat. No. 7,212,869, which was granted on May 1, 2007, incorporated herein by reference in its entirety.

TECHNICAL FIELD

The present invention relates to medical devices and more particularly to means for retaining or preventing dislodgement of an elongate body of a medical device positioned within a body.

BACKGROUND

Medical devices often include a therapy generator and one or more elongated leads, coupled thereto, which are positioned within a patient's body to deliver therapy from the generator. Such therapy may be in the form of electrical stimulation, delivered via electrical conductors extending through a lead body, or fluid infusion, delivered via a lumen extending through a lead body. Some examples of electrical stimulation include pacing and defibrillation; some examples of fluids, which may be infused, include drugs, nutrients, and genetic materials. In many applications, leads are inserted into a cavity or space within a body, for example a blood vessel or an interstitial channel or pocket, formed subcutaneously or submuscularly, where the lead must be retained for a period of time in order to deliver the therapy. Therefore it is desirable to provide lead retention means allowing insertion or forward motion of lead, to position the lead within the space, while preventing retraction or rearward motion of the lead during therapy delivery.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and:

FIG. 3 is a plan view of a lead which may incorporate retention means according to embodiments of the present invention;

FIGS. 5A-B are schematic views of a portion of a lead body including retention means according to yet another embodiment of the present invention;

FIG. 9A is a plan view including a partial section view of another means for retention coupled to the distal portion of the device shown in FIG. 7, according to some alternate embodiments of the present invention; and FIG. 9B is a plan view including a partial section view of another embodiment of the retention means shown in FIG. 9A.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
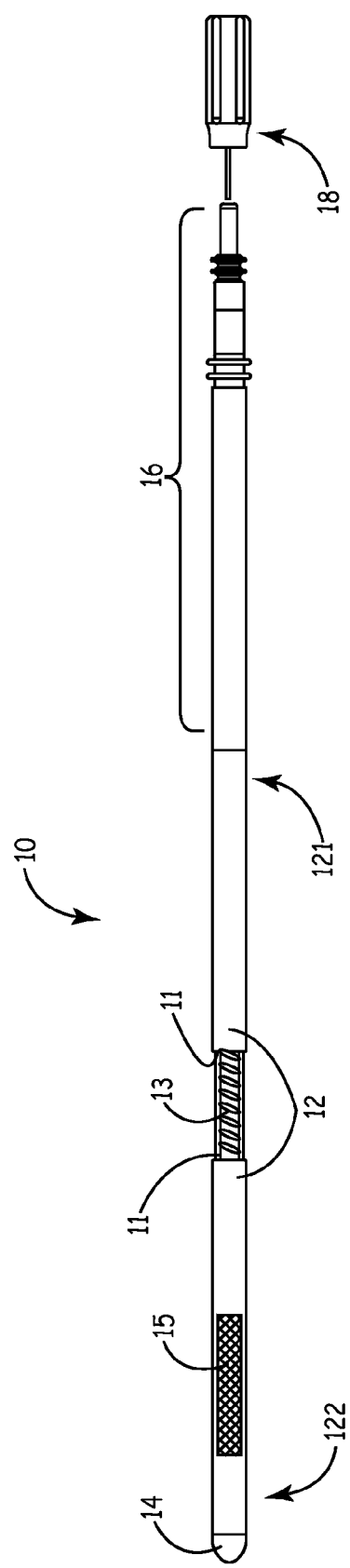
FIG. 1 is a plan view with a partial section of a lead including means for retention according to one embodiment of the present invention.

FIG. 1 is a plan view with a partial section of a lead 10 including means for retention 15 according to one embodiment of the present invention. FIG. 1 illustrates lead 10 including a lead body 12, a connector 16 coupled to a proximal end 121 of the lead body 12 and an electrode 14 coupled to a distal end 122 of the lead body 12; a conductor 13, extending within an outer sheath 11, couples electrode 14 to connector 16, in order to deliver electrical stimulation, and forms a lumen for slideably engaging a stylet 18. Means and materials for constructing such a lead are well known to those skilled in the art.

Figure 6:
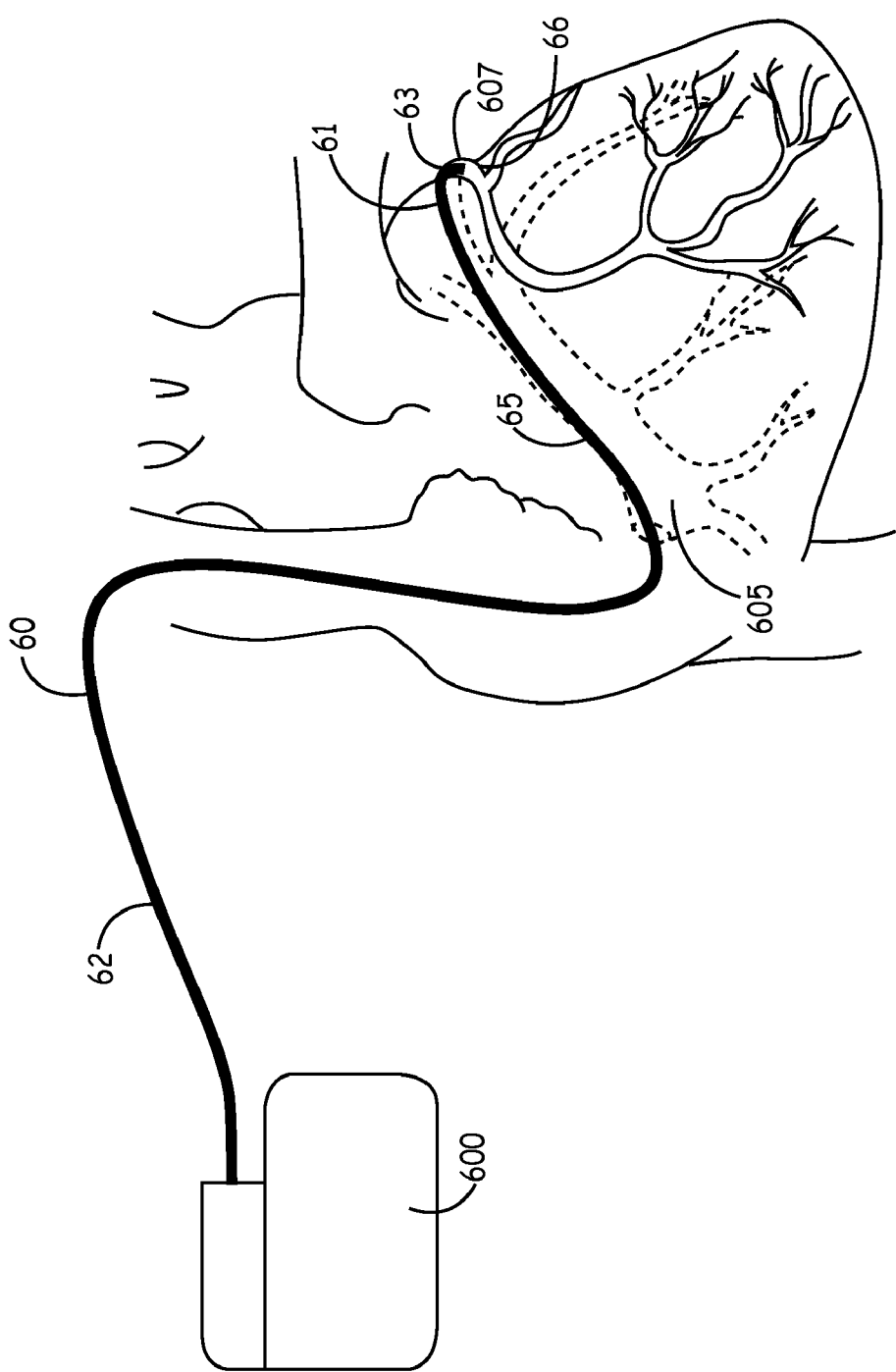
FIG. 6 is a schematic view of a medical device, which may incorporate retention means according to embodiments of the present invention.

FIG. 1 further illustrates retention means 15 formed along an outer surface of lead body 12 in proximity to distal end 122. According to embodiments of the present invention, retention means 15 allows insertion of lead body 12 through a vessel, for example a vessel 607 as illustrated in FIG. 6, while preventing retraction of lead body 12 within the vessel due to an interference of retention means 15 along a wall of the vessel that contacts lead body 12. Retention means according to some embodiments of the present invention extends along a length greater than or equal to approximately 1 mm and may be implemented along any portion of a lead body alone or in conjunction with other retention means; further, retention means 15 may be an integral part of outer sheath 11 or may be formed on a separate collar fitted about lead body 12, either in-line with or about outer sheath 11. Suitable materials for outer sheath 11 and retention means 15 include those that are biocompatible, examples of which include, but are not limited to, silicone and polyurethane.

Figure 2A:
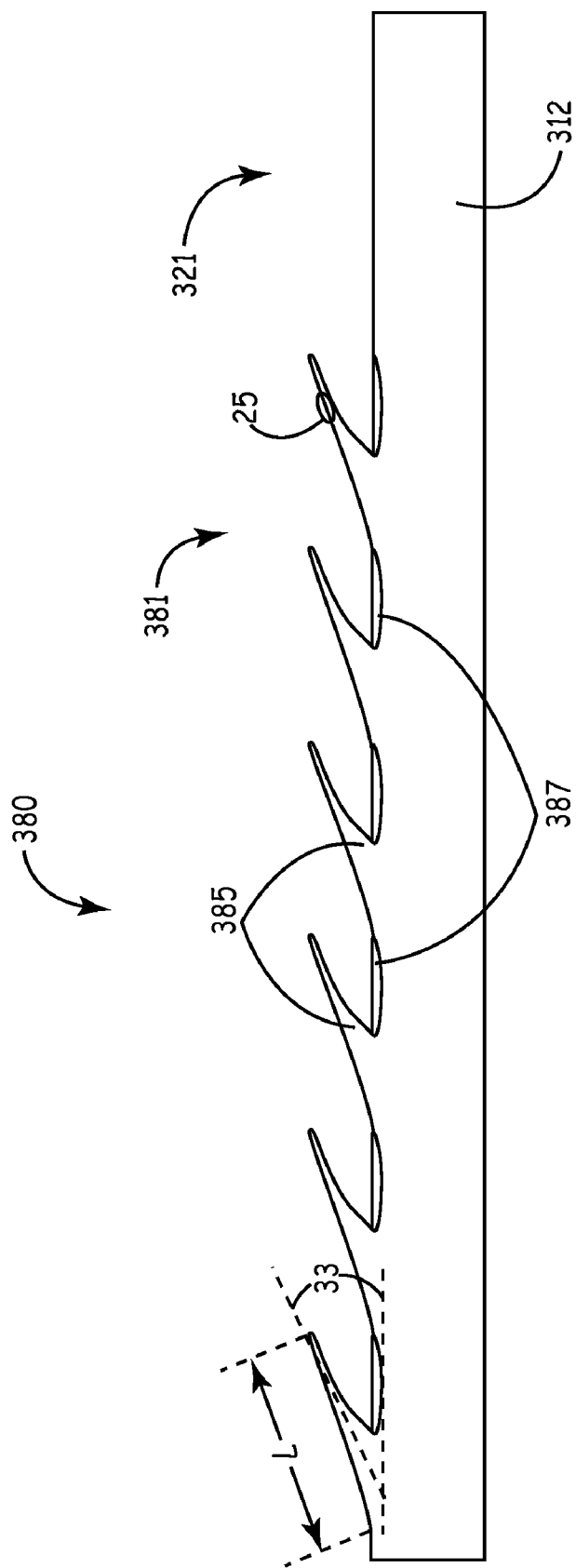
FIG. 2A is an enlarged plan view of a retention means according to one embodiment of the present invention.
Figure 2B:
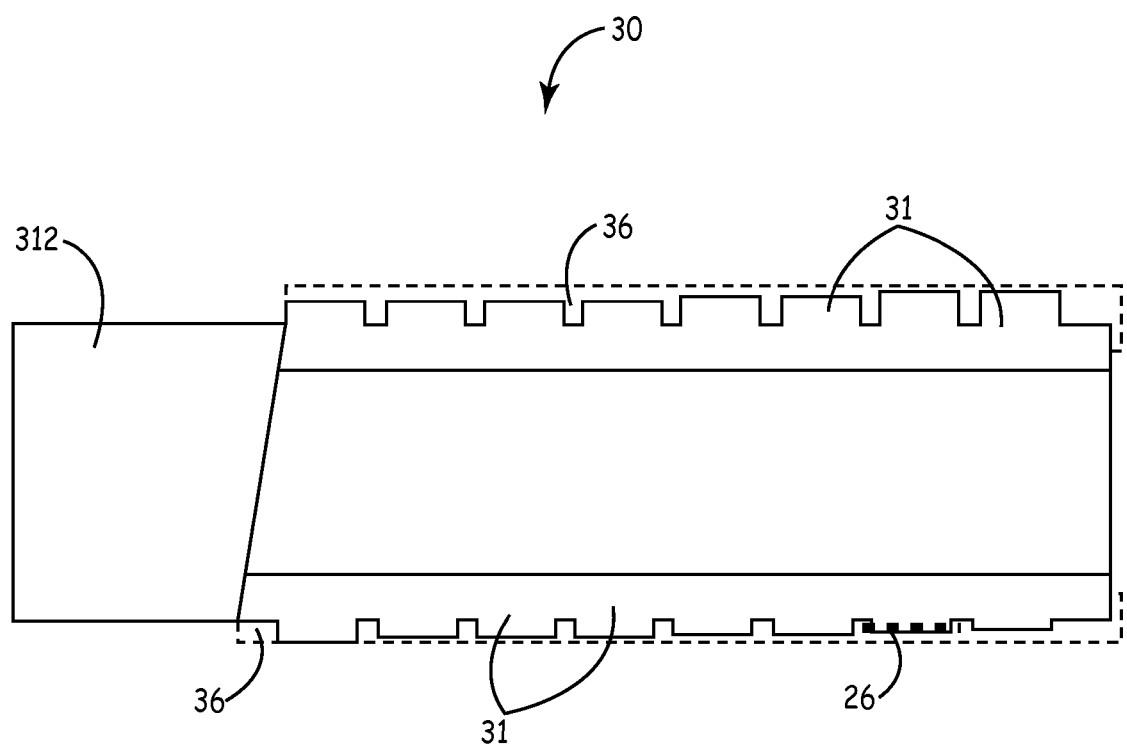
FIG. 2B is an enlarged partial section view of means for retention according to an alternate embodiment.
Figure 2C:
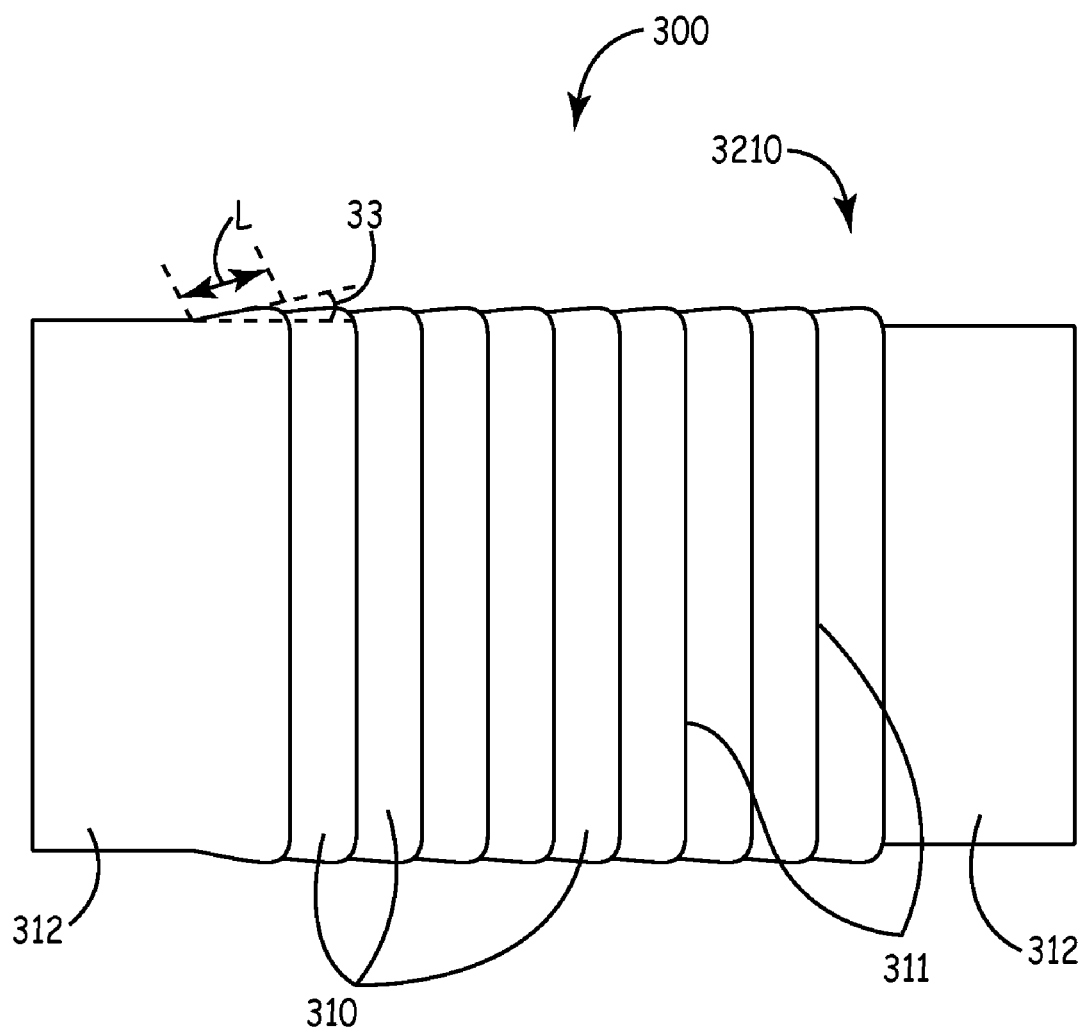
FIG. 2C is an enlarged plan view of means for retention according to another embodiment.
Figure 2D:
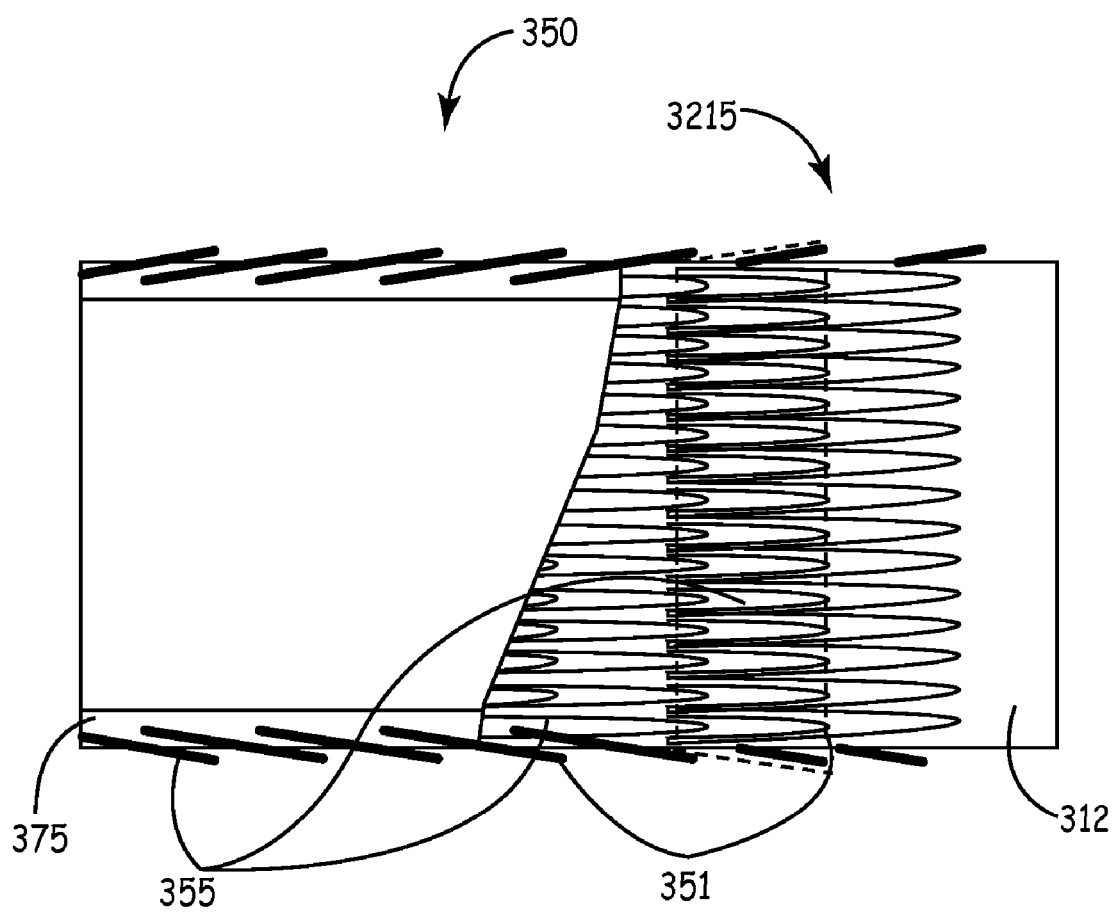
FIG. 2D is an enlarged partial section view of means for retention according to yet another embodiment of the present invention.

Various embodiments of retention means include projections formed along retaining segments as illustrated in FIGS. 2A-D and 4A-5B. It should be noted that alternate embodiments include, but are not limited to, retaining segments extending around an entire circumference of a lead body and segments extending only about a portion of the circumference of the lead body. For example, a plurality of projections may lie in a line, single file, along a length of a retaining segment, as illustrated in FIG. 2A, or each individual projection may extend circumferentially about all or a portion of a retaining segment, as illustrated in FIG. 2C, or a plurality of projections may lie approximately side-by-side about all or a portion of a circumference, as illustrated in FIG. 2D.

In some embodiments, retaining segments as a whole or just the projections may be formed of a bioabsorbable material, examples of which include those taught in lines 10-24 of U.S. Pat. No. 6,173,206. According to these embodiments, if a lead body is chronically implanted, the retaining segment or projections would remain intact long enough to hold the body in place for a period of time up to tissue encapsulation of the body; this may facilitate extraction of a chronically implanted lead. One example of an appropriate bioabsorbable material, polydioxanone is described along with means for molding the material in U.S. Pat. No. 4,490,326, the teachings of which are incorporated by reference herein.

FIG. 2A is an enlarged plan view of means for retention according to one embodiment of the present invention. FIG. 2A illustrates a retaining segment 380 including a plurality of barb-like projections 385 positioned in a single-file line along a length of the segment 380; each of the plurality of projections 385 include a length L and extend laterally from a lead body 312 toward a proximal end 321 at an angle 33, which, according to some embodiments, is less than approximately 45 degrees. According to this embodiment of the present invention and various other embodiments illustrated herein length L is greater than approximately 100 microns. FIG. 2A further illustrates projections 385 as portions of a wall 387 forming retaining segment, having been lifted out of wall 387 according to one embodiment of the present invention. FIG. 2B illustrates an alternate retaining segment 30 extending along a length of lead body 312 and including tread-like projections 31 extending laterally from lead body 312 to form a textured surface adapted to engage a vessel wall, similar to, for example, a sole of a shoe designed to facilitate traction. According to some embodiments of the present invention, projections, i.e. 385, 31, are directly formed in outer surfaces, being integral with a bulk material underlying the surfaces, but, according to alternate embodiments, the projections are formed of separate materials either embedded in or adhered to these surfaces. Alternative methods of forming examples of these embodiments will be described herein below.

FIG. 2B further illustrates retaining segment 30 including a coating 36, which is soluble in body fluids; according to this embodiment, coating 36 fills in around projections 31 and remains intact temporarily, during positioning of lead body 312, so that lead body 312 may be moved back and forth through a vessel if repositioning is necessary. Suitable materials forming coating 36 are soluble in body fluids (within a temperature range encompassing normal body temperature), non-toxic, biocompatible and non-pyrogenic; examples of such a material include sugar derivatives, such as mannitol and dextrose, salts, such as sodium chloride and potassium chloride, and polyvinylpyrrolidone (PVP). Portions of U.S. Pat. No. 4,827,940 teaching methods for forming and applying a mannitol solution are incorporated by reference herein. According to an alternate embodiment, a covering in the form of a thin wall tube may be deployed over retaining segment 30 in place of coating 36. It should be noted that any of the embodiments described herein may include such a coating or a covering facilitating positioning of lead bodies.

FIG. 2C is an enlarged plan view of means for retention according to another embodiment. FIG. 2C illustrates a retaining segment 300 coupled to a portion of lead body 312 and including a proximal end 3210 and a plurality of projections 310, each of which extend around all or a portion of a circumference of lead body 312 and extend laterally from lead body 312 at angle 33 toward proximal end 3210.

FIG. 2D is an enlarged partial section view of means for retention according to yet another embodiment of the present invention. FIG. 2D illustrates a retaining segment 350 including a plurality of fish scale-like projections 355 positioned side-by-side about a circumference of lead body 312 and along a length of segment 350 and including terminal ends 351 directed toward a proximal end 3215. FIG. 2D further illustrates projections 355 as discrete elements embedded in an underlying surface 375 of segment 350 according to one embodiment of the present invention. FIG. 2D also illustrates, by way of a dashed line connecting projections 355 around a circumference, another embodiment in which embedded elements forming projections may be rings or portions of a coil circling a portion of or the entire circumference of segment 350 creating projections similar to projections 310 illustrated in FIG. 2C.

According to further alternate embodiments, some or all projections of a retaining segment, for example projections 385, 31, 310 and 355 (FIGS. 2A-D), each include micro-features further enhancing engagement of the projections with the vessel wall. In FIG. 2A such a feature is illustrated on one of projections 385 as a hole or indentation 25; in FIG. 2B such a feature is illustrated as a modified surface 26 on one of projections 31 wherein surface 26 includes texture, adhesive spots, or some material promoting thrombotic adhesion to vessel wall.

Methods for forming various embodiments of retaining segments, for example those depicted in FIGS. 2A-D, include, but are not limited to, molding, extrusion, cutting, laser ablation, and coating. These methods may form projections directly in outer surfaces, such that they are integral with a bulk material underlying the surfaces, or may integrate the projections with the surface by embedding or adhering.

According to some embodiments of the present invention, transfer or injection molding, using methods known to those skilled in the art, are used to form a retaining segment including projections, examples of which include those depicted in FIGS. 2B-C. According to other embodiments, a cutting process may be used to create projections on a retaining segment, for example segment 380 illustrated in FIG. 2A; a blade may be used to nick the surface or to cut all the way through a wall of the retaining segment.

Alternatively, laser ablation may be used to create projections from a bulk material of a retaining segment, i.e. FIGS. 2B-C, or by exposing, at a surface of the segment, portions of materials which have been embedded within the bulk material underlying the surface during, for example, a molding or extrusion process, i.e. FIG. 2D. U.S. Pat. No. 5,580,699 describes a suitable laser ablation process, which may be used to form retaining segments and the pertinent teachings of the '699 patent are incorporated by reference herein. U.S. Pat. No. 4,272,577 describes an extrusion process for forming ski bases having direction-dependent friction coefficients wherein harder particles, within a plastic matrix flowing through a slit nozzle, become obliquely oriented relative to the surface of the base; in one case, by means of a temperature gradient across the nozzle. We contemplate that similar methods may be developed by those skilled in the art, according to the teachings of the '577 patent, in order to extrude retaining segments according to the present invention, and incorporate by reference the pertinent teachings of the '577 patent herein. Some composite materials suitable for embodiments of the present invention include but are not limited to polyamide and polyimide particles, polyester fibers, carbon fibers or particles and any combination thereof blended with silicone.

According to further alternate embodiments a coating applied to a surface of a retaining segment may form projections and or micro-features on projections, for example similar to those illustrated in FIGS. 2B-C. Stewart et al. describe an example of a suitable coating process via plasma deposition in commonly assigned U.S. Pat. No. 6,549,811, which is incorporated by reference in its entirety herein. Furthermore coatings including particles blended within, for example a silicone medical adhesive including biocompatible metal particles or hard plastic particles may form an embodiment of the present invention for example similar to those illustrated in FIGS. 2B and 2D.

FIG. 3 is a plan view of a lead 40, which may incorporate retention means according to embodiments of the present invention. FIG. 3 illustrates lead 40 including a proximal portion 43, a first preformed bend 41 extending from proximal portion 43 to an intermediate segment 45 and a second preformed bend 42 extending from intermediate segment 45 to distal segment 46, which is terminated by a tip 44. Such a lead is fully described in commonly assigned U.S. Pat. No. 5,999,858, which is herein incorporated by reference in its entirety. According to embodiments of the present invention, first and second bends 41 and 42 acting as means for retention of lead body in a coronary vessel, for example a coronary sinus 605 or a branch vessel 607 thereof illustrated in FIG. 6, are supplemented by any of the retaining segments described herein, which may be formed along the lead body surface at first bend 41, intermediate segment 45, second bend 42, distal segment 46, or any combination thereof. Any other combination of bends within a lead body is within the scope of the present invention.

Figure 4A:
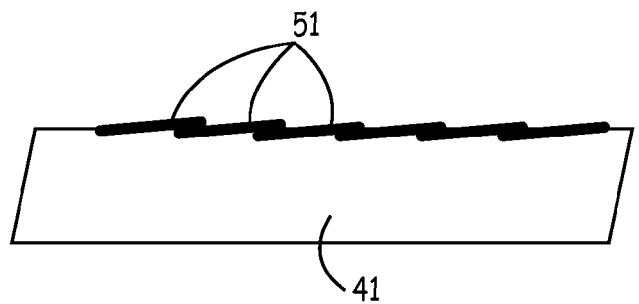
FIGS. 4A-B are plan views of a portion of a lead body including retention means according to an alternate embodiment of the present invention.
Figure 4B:
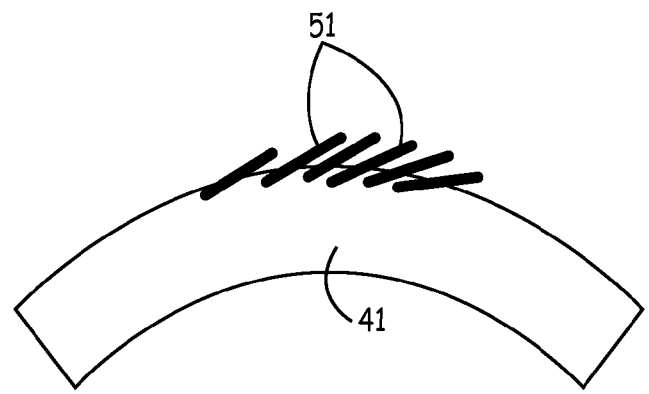

FIGS. 4A-B are partial plan views of one embodiment of lead 40 showing only a portion at first bend 41, which includes a retaining segment formed by projections 51. According to some embodiments of the present invention a retaining segment may be activated by a bending of a lead body as illustrated in FIGS. 4A-B. If a stylet, for example stylet 18 shown in FIG. 1, is inserted into lead 40 to straighten preformed bend 41, projections 51 become approximately parallel with an outer surface of lead 40, as illustrated in FIG. 4A. Once the stylet is removed preformed bend 41 reforms such that projections 51 protrude laterally and are thus activated to prevent rearward motion of lead 40 within a vessel. If it becomes necessary to reposition lead 40, the stylet may be reinserted to straighten bend 41 thus bringing projections into approximate alignment with the surface of lead 40. It should be noted that the embodiment illustrated in FIG. 2D may be of the type illustrated in FIGS. 4A-B.

FIG. 3 further illustrates lead 40 including an anchoring sleeve 48 positioned about proximal portion 43 thereof. According to an additional embodiment of the present invention, means for retention as illustrated herein, may be formed along an outer surface of proximal portion to provide frictional forces complementing anchoring sleeve 48 at a venous entry point. The means for retention may either engage an inner surface of anchoring sleeve 48 or engage a vein wall in proximity to the entry point.

FIGS. 5A-B schematic views of a portion of a lead body including retention means according to yet another embodiment. FIGS. 5A-B illustrate a lead body 20 including a plurality of hair-like projections or fibers 205 each attached at one end to lead body 20 and directed by their attachment points 23 to extend out from and along a length of body 20 toward a proximal end 221 of body 20. According to the illustrated embodiment, as lead body 20 is advanced distally in a vessel 207 per arrow A, as in FIG. 5A, projections 205 are suspended proximally; when lead body 20 is retracted proximally per arrow B, as in FIG. 5B, projections 205 are forced toward a distal end 222 of body 20 to become bunched up and wedged between body 20 and a wall of vessel 207, thereby providing retention means for lead body 20. Projections may be formed from a bioabsorbable polymer, for example polyglyocolic acid or polylactic acid. Alternately projections 205 may be formed from polyester fibers or some other material promoting thrombotic adhesion with the vessel wall to enhance retention within vessel 207; such thrombotic projections may include a non-thrombogenic coating adapted to dissolve after the lead is positioned per FIG. 5B, examples of which include a benzalkonium chloride-heparin solution and polyvinylpyrrolidone. Projections 205 may be attached at attachment points 23 by embedment within lead body 20 or by adhesive attachment, for example by means of silicone medical adhesive.

FIG. 6 is a schematic view of an exemplary medical device, which may incorporate retention means according to embodiments of the present invention. FIG. 6 illustrates the medical device including a therapy generator 600 coupled to a lead 60 implanted within branch vessel 607 emanating from coronary sinus 605. Lead 60, which includes a connector terminating a proximal portion 62, an electrode in proximity to a distal end 66 and a conductor extending through an outer insulative sheath (similar to lead 10 illustrated in FIG. 1), may deliver electrical therapy, or may deliver infusions of therapeutic fluids from generator 600 through a central lumen. FIG. 6 further illustrates potential retention segment sites 65, 61, and 63 along lead 60 where projections of retention segments according to embodiments of the present invention would engage a wall of vessels 605 and 607 to prevent rearward dislodgment of lead 60 from vessel 607.

Figure 7:
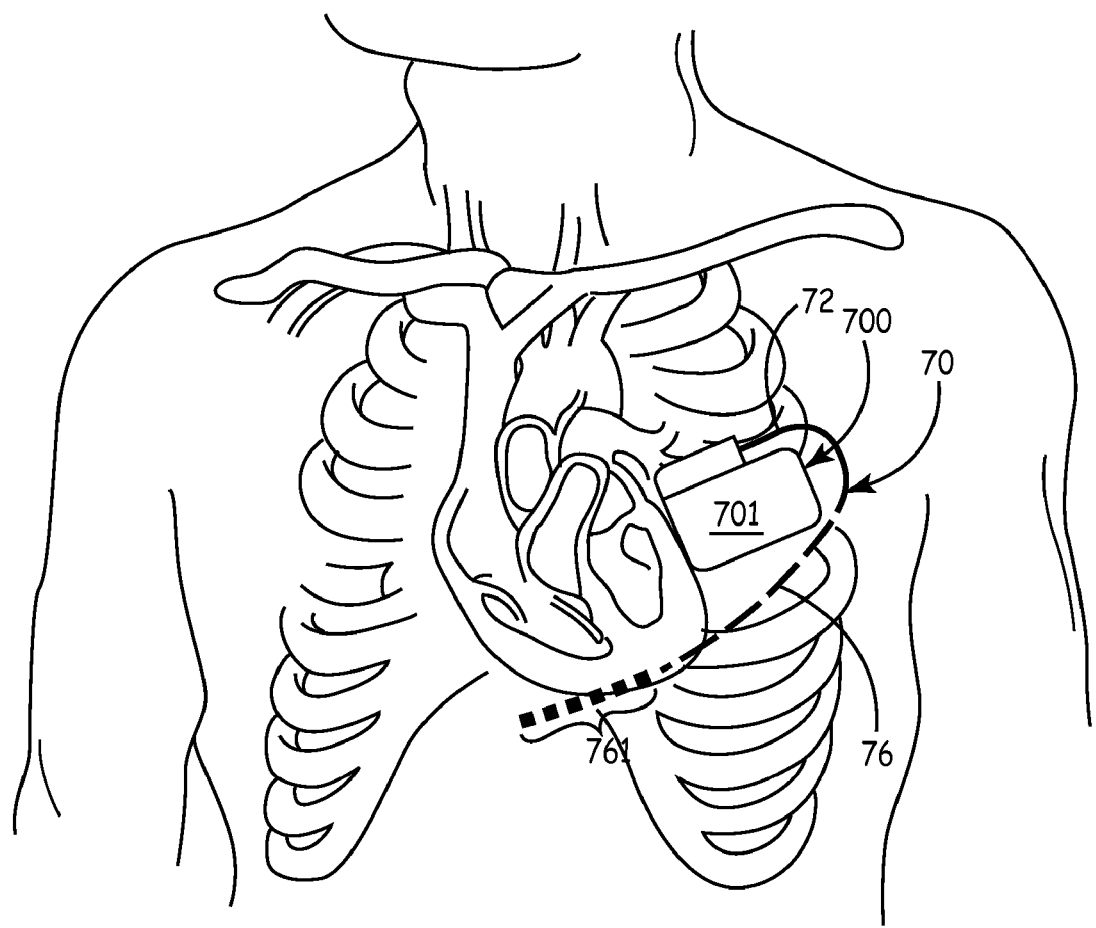
FIG. 7 is a schematic view of another exemplary medical device which may incorporate retention means according to embodiments of the present invention.

FIG. 7 is a schematic view of another exemplary medical device which may incorporate retention means according to embodiments of the present invention; the device is shown implanted subcutaneously in a patient, exterior to the patient's rib cage, or extra-thoracic. FIG. 7 illustrates the system including a therapy generator 700 and an elongate medical electrical lead body 70 coupled thereto by means of a connector (not shown), which terminates a proximal portion 72 of lead body 70. According to the illustrated embodiment, the device is positioned to deliver cardiac stimulation, for example, a defibrillation shock, via a pair of electrodes, wherein a first electrode of the pair is formed by a housing 701 of generator 700 and a second electrode of the pair is formed by a conductor coil 761 coupled to a distal portion 76 of lead body 70; generator 700 is shown implanted along an anterior chest wall, in a subcutaneous or sub-pectoral location, on a first side of the heart (an outline of which is shown), and lead body distal portion 76 is shown, with dashed lines, implanted on an opposite side of the heart having been tunneled through the subcutaneous tissue surrounding the rib cage toward a posterior side of the patient. It is desirable to fix coil 761 at the illustrated location, as close to the spine as possible, so that an electric field of a shock delivered between housing 701 and coil 761 traverses a maximum amount of left ventricular myocardium for the lowest possible defibrillation threshold. Various embodiments of fixation means coupled to lead body distal portion 76 are described below in conjunction with FIGS. 8 and 9A-B. It should be noted that the embodiments of FIGS. 8 and 9A-B may also be incorporated by lead bodies intended for venous implant, for example, as described above and illustrated in FIG. 6, but are not necessarily limited by any particular implant location or any particular application, such as those described in conjunction with FIGS. 6 and 7.

Figure 8:
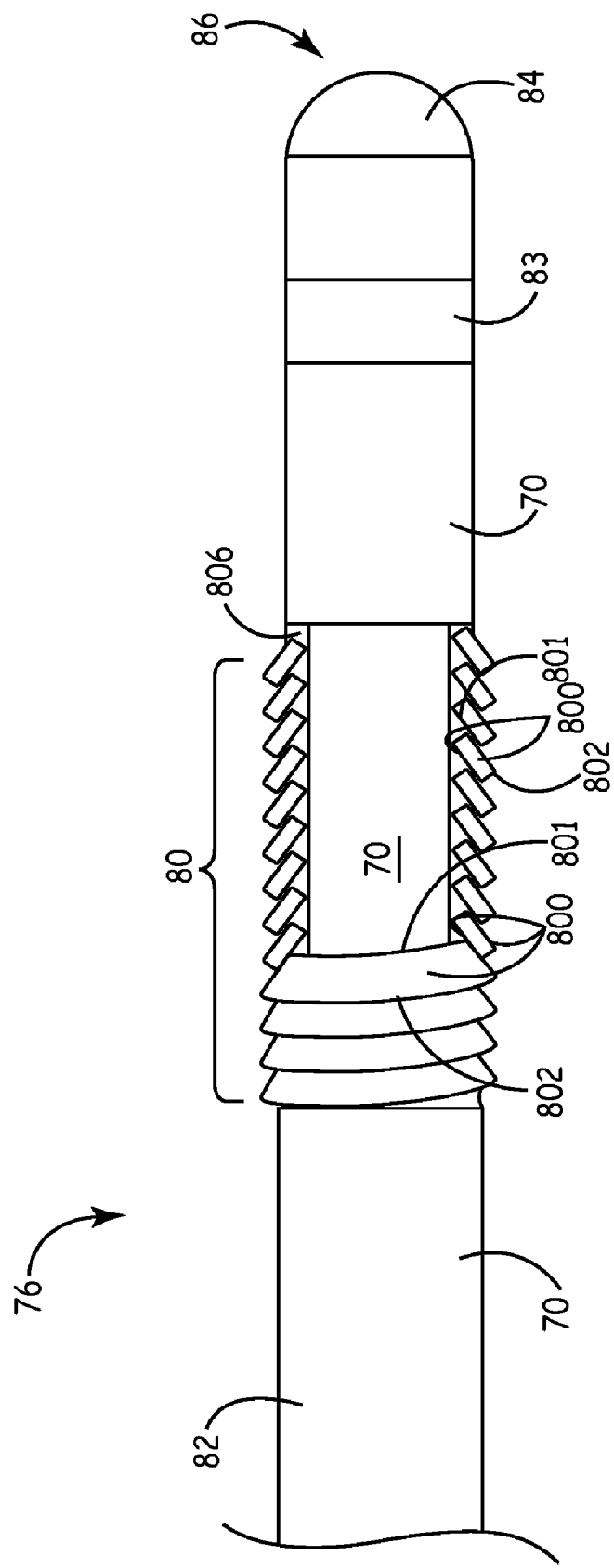
FIG. 8 is a plan view including a partial section view of a means for retention coupled to a distal portion of the device shown in FIG. 7, according to some embodiments of the present invention.

FIG. 8 is a plan view including a partial section view of lead body distal portion 76, according to some embodiments of the present invention. FIG. 8 illustrates distal portion 76 including a coil 80 and a ring electrode 83 coupled to lead body 70 and a tip electrode 84 terminating a distal end 86 of lead body 70. Electrodes 83 and 84 may be used for pacing and sensing, being coupled, via elongate conductors (not shown) extending within lead body 70, to corresponding connector contacts mounted to proximal portion 72 (FIG. 7), but are not necessary components for embodiments of the present invention. According to preferred embodiments of the present invention, coil 80 functions as a high voltage electrode to provide defibrillation therapy, for example, in conjunction with the housing of generator 700, as previously described in conjunction with FIG. 7, and is likewise coupled to a corresponding proximal connector contact via an elongate conductor (not shown) extending within lead body 70.

FIG. 8 further illustrates coil 80 formed from a wire having a rectangular cross-section wherein a side, or surface 800 of the wire extends at an angle, with respect to a longitudinal axis of body 70, from a first edge 801 to a second edge 802, toward a proximal end 82 of body 70. According to the illustrated embodiment, first edge 801 of surface 800 is in close proximity to body 70, and may be embedded therein, while second edge 802 of surface 800, being spaced apart from body 70, projects out therefrom. Angled surface 800 allows for forward motion of distal portion 76, with tip electrode 84 as the leading edge, to facilitate an implantation of distal portion 76 within a vessel or an interstitial pocket or tunnel, while projecting edge 802 acts to retain distal portion 76 by interacting with surrounding body tissue to prevent retrograde motion of distal portion 76.

FIG. 8 shows body 70 including an optional backfill material 806 adhered thereto and surrounding the turns of coil 80, for example, silicone rubber injected between the turns of coil 80, however, coil 80 may be embedded directly within body 70, for example, via thermoforming or injection molding methods known to those skilled in the art. The wire of coil 80 may be formed from any suitable resilient biocompatible material; according to those embodiments in which coil 80 functions as an electrode, the wire is preferably formed from tantalum or a platinum iridium alloy.

FIG. 9A is a plan view including a partial section view of lead body distal portion 76 including alternate retention means, according to some embodiments of the present invention. FIG. 9A illustrates distal portion 76 including a coil 90 in place of coil 80 shown in FIG. 8. According to FIG. 9A, coil 90 is formed by a wire 95, which has a round cross-section, and a relatively flat strip 97 coupled thereto; a surface 900 of strip 97 extends at an angle, with respect to the longitudinal axis of lead body 70, from a first edge 901 to a second edge 902, toward proximal end 82. Angled surface 900 of coil 90 allows forward passage, as previously described for coil 80, while second edge 902, which projects out from body 70, can act to retain distal portion 76 at an implant site by preventing retrograde motion of portion 76. According to preferred embodiments of the present invention, at least wire 95 is conductive, for example, formed from tantalum or a platinum iridium alloy, and acts as a high voltage electrode. Strip 97 may be formed from any suitable resilient and biocompatible material being wound in conjunction with wire 95, or being wound separately from wire 95 and interlaced therewith, following winding. Suitable methods for bonding strip 97 to wire 95 include those known in the art and may include adhesive bonding, ultrasonic welding, resistance welding and laser welding; the bonding may take place either prior to or following winding.

FIG. 9B is a plan view including a partial section view of another embodiment of the retention means shown in FIG. 9A. FIG. 9B illustrates a coil 90' being similar to coil 90 with the exception of strip 97', which includes a first edge 901' and a second, serrated edge 902'. It should be noted that, although strips 97 and 97' are shown extending alongside an entire length of coils 90, 90', respectively, the invention is not so limited and, according to additional alternate embodiments, one or more shorter strips may extend along one or more discrete portions of coils 90, 90'. Furthermore, strips 97, 97', or shorter strip embodiments, may be formed from any of the previously referenced bioabsorbable materials, remaining intact long enough to hold distal portion 76 in place for tissue encapsulation.

Although embodiments of the present invention are described in the context of therapy delivery, diagnostic devices adapted for insertion within a vessel or interstitial space of a body may also incorporate retention means described herein and thus fall within the scope of the present invention. In the foregoing detailed description, the invention has been described with reference to specific embodiments. However, it may be appreciated that various modifications and changes can be made without departing from the scope of the invention as set forth in the appended claims.

I claim:

1. A medical device, comprising:
an elongate lead body including a proximal end and a distal end; and
a coil extending along a length of the body between the proximal and distal ends and including a surface having a first edge and a second edge, the first edge extending along a helical path of the coil, wherein the surface of the coil projects away from the lead body at an angle, with respect to a longitudinal axis of the lead body, from the first edge to the second edge, toward the proximal end of the lead body, and wherein the first edge of the surface is disposed in close proximity to the lead body and the second edge of the surface is spaced apart from the lead body wherein the coil comprises a conductive wire and a relatively flat strip coupled together, wherein the surface is formed by the strip, and wherein the coil surface is adapted to interact with surrounding body tissue to prevent retrograde motion of the distal end of the lead body.

2. The device of claim 1, wherein the second edge of the surface extends along the helical path of the coil.

3. The device of claim 1, wherein the second edge of the surface is serrated.

4. The device of claim 1, wherein the conductive wire includes an electrode surface adjacent the strip.

5. The device of claim 1 wherein the strip comprises a bioabsorbable material.

6. The device of claim 1, wherein the first edge of the surface is fixedly engaged with the lead body.

7. A medical device, comprising:
an elongate lead body having a longitudinal axis and including a proximal end and a distal end; and
a coil comprising a coiled strip extending along a length of the body between the proximal and distal ends and including a side surface having a first edge and a second edge, the first edge extending along a helical path of the coil, wherein the side surface of the coil, when seen in a cross section taken along the longitudinal axis, projects away from the lead body at an angle, with respect to the longitudinal axis of the lead body and extends toward the proximal end of the lead body from the first edge to the second edge and wherein the first edge of the side surface is disposed in close proximity to the lead body and the second edge of the surface is spaced apart from the lead body, wherein the side surface comprises and electrode surface and wherein the coiled strip is adapted to interact with surrounding body tissue to prevent retrograde motion of the distal end of the lead body.

8. A medical device, comprising:
an elongate lead body including a proximal end and a distal end;
a coiled wire having proximal and distal ends; and
a coiled fixation strip including a first edge and a second edge, the first edge of the strip being disposed in close proximity to the lead body and the second edge of the strip being spaced apart from the body, wherein the wire extends adjacent to the fixation strip along a helical path extending along a portion of the lead body between the proximal and distal ends of the coiled wire, and wherein the fixation strip projects away from the lead body at an angle, with respect to a longitudinal axis of the lead body, from the first edge to the second edge, toward the proximal end of the lead body wherein the coiled fixation strip is adapted to interact with surrounding body tissue to prevent retrograde motion of the distal end of the lead body.

9. The device of claim 8, wherein the second edge of the strip is serrated.

10. The device of claim 8, wherein the first edge of the strip is fixedly engaged with the body.

11. The device of claim 8, wherein the wire includes an electrode surface adjacent the strip.

12. The device of claim 8, wherein the wire and the strip are bonded together.

13. The device of claim 8, wherein the strip comprises a bioabsorbable material.

14. A medical electrical defibrillation lead, comprising:
an elongate lead body having a longitudinal axis and including a proximal end and a distal end; and
a coiled defibrillation electrode comprising a coiled strip extending along a length of the body between the proximal and distal ends and including a side surface having a first edge and a second edge, the first edge extending along a helical path of the defibrillation electrode, wherein the side surface of the coiled defibrillation electrode when seen in a cross section taken along the longitudinal axis and projects away from the lead body toward the proximal end of the lead body at an angle, with respect to the longitudinal axis of the lead body, from the first edge to the second edge, and wherein the first edge of the side surface is disposed in close proximity to the lead body and the second edge of the side surface is spaced apart from the lead body and wherein the coiled strip is adapted to interact with surrounding body tissue to prevent retrograde motion of the distal end of the lead body.

15. The lead of claim 14, wherein the second edge of the surface extends along the helical path of the coiled defibrillation electrode.

16. The lead of claim 14, wherein the coiled defibrillation electrode comprises a wire and a relatively flat strip fixedly engaged with the wire, and wherein the surface is formed by the strip.

17. The lead of claim 16, wherein the second edge of the surface is serrated.

18. The lead of claim 16, wherein the strip comprises a bioabsorbable material.

19. The lead of claim 14, wherein the first edge of the surface is fixedly engaged with the lead body.

* * * * *